(12) United States Patent
Miyauchi (10) Patent No.: US 10,336,979 B2
(45) Date of Patent: Jul. 2, 2019

(54) SPECIMEN PROCESSING SYSTEM AND METHOD FOR PROCESSING SPECIMEN

(71) Applicant: Kabushiki Kaisha Yaskawa Denki, Kitakyushu-shi (JP)

(72) Inventor: Kohei Miyauchi, Kitakyushu (JP)

(73) Assignee: KABUSHIKI KAISHA YASKAWA DENKI, Kitakyushu-shi (JP)

( * ) Notice: Subject to any disclaimer, the term of this patent is extended or adjusted under 35 U.S.C. 154(b) by 18 days.

(21) Appl. No.: 15/255,797

(22) Filed: Sep. 2, 2016

(65) Prior Publication Data
US 2017/0073631 A1 Mar. 16, 2017

(30) Foreign Application Priority Data

Sep. 11, 2015 (JP) ................. 2015-180196

(51) Int. Cl.
| | | |
|---|---|---|
| C12M 1/36 | (2006.01) | |
| C12M 1/22 | (2006.01) | |
| C12M 1/00 | (2006.01) | |
| C12M 1/26 | (2006.01) | |
| B25J 9/00 | (2006.01) | |
| G01N 35/02 | (2006.01) | |
| G01N 35/00 | (2006.01) | |

(52) U.S. Cl.
CPC ............ *C12M 41/48* (2013.01); *B25J 9/0087* (2013.01); *C12M 23/10* (2013.01); *C12M 33/00* (2013.01); *C12M 47/02* (2013.01); *G01N 35/0099* (2013.01)

(58) Field of Classification Search
CPC ...... C12M 23/10; C12M 33/00; C12M 41/48; C12M 47/02; G01N 35/0099; G06K 2209/01; G06K 9/2054
See application file for complete search history.

(56) References Cited

U.S. PATENT DOCUMENTS

| | | |
|---|---|---|
| 2007/0106422 A1 | 5/2007 | Jennings et al. |
| 2014/0106386 A1 | 4/2014 | Umeno et al. |

FOREIGN PATENT DOCUMENTS

| | | |
|---|---|---|
| EP | 1 661 980 A1 | 5/2006 |
| EP | 2 687 855 A1 | 1/2014 |

(Continued)

OTHER PUBLICATIONS

Extended European Search Report dated Feb. 8, 2017 in Patent Application No. 16187942.4.

(Continued)

*Primary Examiner* — Gautam Prakash
*Assistant Examiner* — Lydia Edwards
(74) *Attorney, Agent, or Firm* — Oblon, McClelland, Maier & Neustadt, L.L.P.

(57) ABSTRACT

A specimen processing system includes a culture vessel, a spatula, a robot, and a robot controller. The culture vessel is open on a top surface and includes a circular culture surface on which cells are culturable. The spatula includes a blade to remove the cells off the culture surface. The robot includes a hand to hold the culture vessel and/or the spatula. The robot controller includes an operation controller to control the robot to: move the spatula relative to the culture vessel with a first end of the blade on a circumference of the culture surface to remove first cells that are nearer the circumference of the culture surface; and move the spatula relative to the culture vessel to remove second cells that are inner than the first cells on the culture surface.

20 Claims, 8 Drawing Sheets

(56) References Cited

FOREIGN PATENT DOCUMENTS

| EP | 2 728 363 A1 | 5/2014 |
|---|---|---|
| EP | 2 733 196 A1 | 5/2014 |
| EP | 2 745 997 A1 | 6/2014 |
| EP | 2 960 739 A2 | 12/2015 |
| JP | 2013-9618 A | 1/2013 |
| JP | 2014-113062 | 6/2014 |
| WO | WO 2006/093652 A2 | 9/2006 |

OTHER PUBLICATIONS

Alois Knoll et al., "Flexible Automation of Cell Culture and Tissue Engineering Tasks", Biotechnology Progress, vol. 20, No. 6, XP55166246, Dec. 3, 2004, pp. 1825-1835.
Office Action dated Dec. 19, 2017 in Japanese Patent Application No. 2015-180196 with English translation, 7 pages.

SPECIMEN PROCESSING SYSTEM AND METHOD FOR PROCESSING SPECIMEN

CROSS-REFERENCE TO RELATED APPLICATIONS

The present application claims priority under 35 U.S.C. § 119 to Japanese Patent Application No. 2015-180196, filed Sep. 11, 2015. The contents of this application are incorporated herein by reference in their entirety.

BACKGROUND

Field of the Invention

The embodiments disclosed herein relate to a specimen processing system and a method for processing a specimen.

Discussion of the Background

In biomedical fields, robots are used in specimen processing such as injection, agitation, and separation of reagents.

Japanese Unexamined Patent Application Publication No. 2013-0096118 discloses using a robot to remove cells off a culture surface on a culture vessel such as a dish using a spatula such as a cell scraper.

SUMMARY

According to one aspect of the present disclosure, a specimen processing system includes a culture vessel, a spatula, a robot, and a robot controller. The culture vessel is open on a top surface of the culture vessel and includes a culture surface which has a circular shape and on which cells are culturable. The spatula includes a blade to remove the cells off the culture surface. The robot includes a hand to hold at least one of the culture vessel and the spatula. The robot controller is configured to control the robot and includes an operation controller. The operation controller is configured to control the robot to perform: a first operation to move the spatula relative to the culture vessel with a first end of the blade on a circumference of the culture surface so as to remove first cells among the cells on the culture surface that are nearer the circumference of the culture surface; and a second operation to move the spatula relative to the culture vessel so as to remove second cells among the cells on the culture surface that are inner than the first cells on the culture surface.

According to another aspect of the present disclosure, a specimen processing system includes a culture vessel, a spatula, a robot, and a robot controller. The culture vessel is open on a top surface of the culture vessel and includes a culture surface which has a circular shape and on which cells are culturable. The spatula includes a blade to remove the cells off the culture surface. The robot includes a hand to hold at least one of the culture vessel and the spatula. The robot controller is configured to control the robot and includes an operation controller. The operation controller is configured to control the robot to move the spatula relative to the culture vessel while keeping the blade inclined relative to a radial direction of the culture vessel with a first end of the blade on a circumference of the culture surface and with a second end of the blade displaced from the radial direction relative to the first end of the blade so as to remove first cells among the cells on the culture surface that are nearer the circumference of the culture surface.

According to the other aspect of the present disclosure, a method is for processing a specimen using a culture vessel, a spatula, a robot, and a robot controller. The culture vessel is open on a top surface of the culture vessel and includes a culture surface which has a circular shape and on which cells are culturable. The spatula includes a blade to remove the cells off the culture surface. The robot includes a hand to hold at least one of the culture vessel and the spatula. The robot controller is configured to control the robot. The method includes controlling the robot to move the spatula relative to the culture vessel with a first end of the blade on a circumference of the culture surface so as to remove first cells among the cells on the culture surface that are nearer the circumference of the culture surface. The robot is controlled to move the spatula relative to the culture vessel so as to remove second cells among the cells on the culture surface that are inner than the first cells on the culture surface.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings. In the following description, what is called a two-arm robot has its two arms cooperate with each other to perform specimen processing. A two-arm robot, however, is not intended in a limiting sense; it is also possible to use a single-arm robot. It is noted that the following embodiments are provided for exemplary purposes only and are not intended in a limiting sense.

Also in the following description, the terms "parallel", "perpendicular", and "vertical" may occasionally be used to not only mean "parallel", "perpendicular", and "vertical", respectively, in a strict sense but also mean "parallel", "perpendicular", and "vertical", respectively, in an approximate sense. That is, the terms "parallel", "perpendicular", and "vertical" are used taking into consideration production-related, installation-related, processing-related, and detection-related tolerances and errors.

Figure 1:
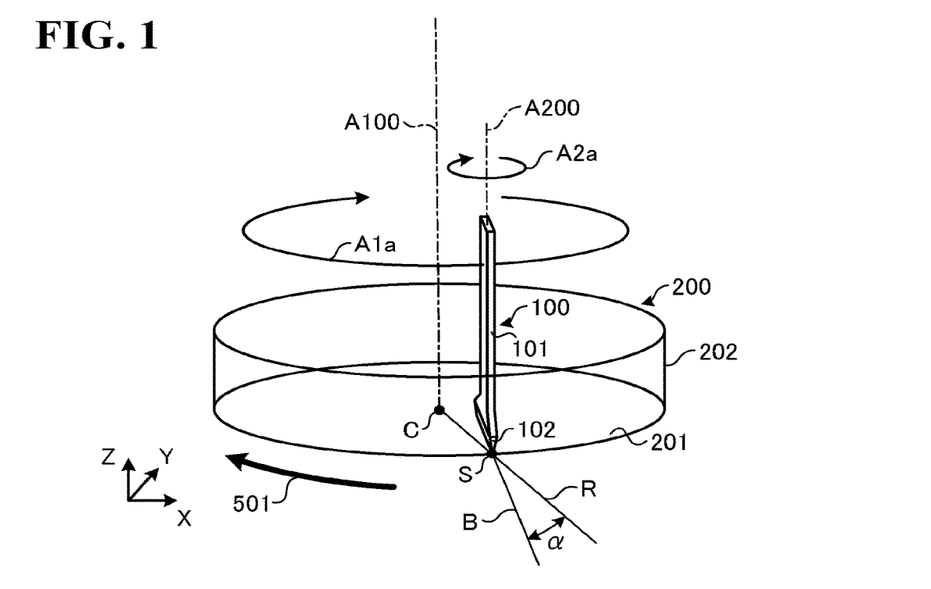
FIG. 1 is a schematic illustrating a method for processing a specimen.

First, a method according to this embodiment for processing a specimen will be described by referring to FIG. 1. FIG. 1 is a schematic illustrating the method according to this embodiment for processing a specimen. For ease of description, FIG. 1 illustrates a three-dimensional orthogonal coordinate system including X axis, Y axis, and Z axis. Z axis has its positive direction oriented in a vertically upward direction from the center C of a culture surface 201 of a culture vessel 200. X axis and Y axis are parallel to the culture surface 201. This orthogonal coordinate system may also be illustrated in some other drawings referred to in the following description.

As illustrated in FIG. 1, a spatula 100 is a cell scraper, for example, and includes a handle 101 and a blade 102. The blade 102 is disposed at one end of the handle 101. The handle 101 is holdable by hands 30 (described later by referring to FIG. 3). The blade 102 is made of an elastic material. When the blade 102 is pressed into full contact with the culture surface 201 and moved in a forward direction 501, in which the spatula 100 moves, the blade 102 bends in the backward direction opposite to the forward direction 501 while keeping close contact with the culture surface 201. The blade 102 may have any shape insofar as full contact with the culture surface 201 is established. The handle 101 and the blade 102 may be separate parts or an integral part.

The culture vessel 200 is a dish, for example, and includes the culture surface 201 and a surrounding wall 202. The culture surface 201 has a circular shape. On the culture surface 201, cells are cultured. The surrounding wall 202 has a hollow cylindrical shape standing on the circumference of the culture surface 201. The top surface of the culture vessel 200 (the surface in the Z-axis positive direction) is open.

As illustrating FIG. 1, reference letter S denotes the start position of the removal operation along the circumference of the culture surface 201, reference letter B denotes an imaginary line extended from the blade 102, reference letter R denotes an imaginary radial-direction line connecting between center C and start position S, and reference letter α denotes the angle formed by line B and line R. Start position S is the position at which a first end of the blade 102 contacts with the circumference of the culture surface 201 (the inner side of the surrounding wall 202).

By holding the spatula 100 and the culture vessel 200 using the hands 30, described later, and moving the spatula 100 and the culture vessel 200 relative to each other, the above-described cell removal operation is performed. The method according to this embodiment for processing a specimen will be described in detail below.

As illustrated in FIG. 1, in the method according to this embodiment for processing a specimen, those cells that are nearer the circumference of the culture surface 201 of the culture vessel 200 are first to be removed with the length of the blade 102 of the spatula 100 inclined relative to line R.

In the embodiment of FIG. 1, in top view of the culture vessel 200, the length of the blade 102 (see line B) is inclined clockwise by angle α relative to line R, which is a radial line passing through the start position S. That is, in the embodiment of FIG. 1, the center C-side end of the blade 102 falls behind in the backward direction opposite to the forward direction 501. The spatula 100 makes one revolution along the circumference of the culture surface 201 while keeping the blade 102 inclined at an angle of α. Angle α may be any angle greater than zero degree.

Specifically, as illustrated in FIG. 1, the spatula 100 makes orbital rotation about center line A100 of the culture vessel 200 (see direction A1a illustrated in FIG. 1) while rotating itself about rotation axis A200 (see direction A2a illustrated in FIG. 1). Here, the spatula 100 makes one rotation about itself per orbital rotation, and this enables the removal operation to be performed with the blade 102 inclined at an angle of α.

A conventional removal operation to remove cells nearer the circumference of the culture surface 201 involves keeping angle α at 0 degree. That is, in the conventional removal operation, the length of the blade 102 is perpendicular to the circumference of the culture surface 201. This causes a portion of the blade 102 contacting the surrounding wall 202 to be deformed by frictional force, creating a gap between the blade 102 and the surrounding wall 202 and allowing removed cells to leak through the gap in the backward direction opposite to the forward direction 501.

In view of this situation, in the method according to this embodiment for processing a specimen, cells nearer the circumference of the culture surface 201 are removed with the length of the blade 102 of the spatula 100 being inclined relative to the forward direction 501, as illustrated in FIG. 1. This configuration eliminates or minimizes occurrence of a gap between the blade 102 and the surrounding wall 202, resulting in improved cell collection efficiency.

As illustrated in FIG. 1, a second end of the blade 102 (the end nearer the center C) is displaced from the radial direction of the culture vessel 200 relative to the first end of the blade 102 (the end on the surrounding wall 202) in the backward direction opposite to the forward direction 501. In the following description, this posture of the spatula 100 will be hereinafter referred to as "outer-end leading posture", and a removal operation performed in this posture will be hereinafter referred to as "removal operation in outer-end leading posture". The removal operation in outer-end leading posture will be detailed later by referring to FIG. 4A and other drawings.

It is noted that in the method according to this embodiment for processing a specimen, the removal operation may be performed with the spatula 100 in such a posture that the second end of the blade 102 (the end nearer the center C) is displaced from the radial direction of the culture vessel 200 relative to the first end of the blade 102 (the end on the surrounding wall 202) in the forward direction 501.

In the following description, this posture of the spatula 100 will be hereinafter referred to as "inner-end leading posture", and a removal operation performed in this posture will be hereinafter referred to as "removal operation in inner-end leading posture". The removal operation in inner-end leading posture will be detailed later by referring to FIG. 8A and other drawings.

Figure 2:
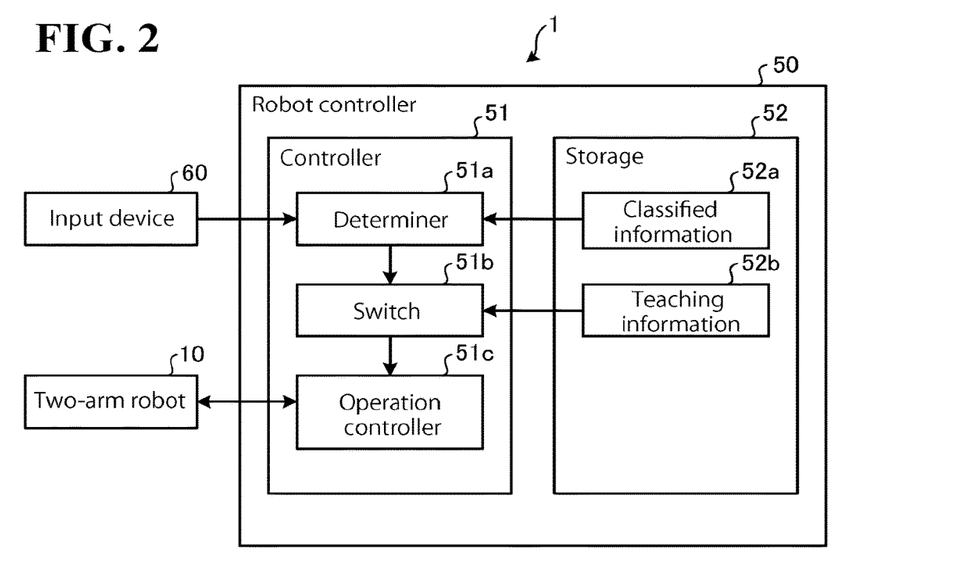
FIG. 2 is a block diagram illustrating a configuration of a specimen processing system.

By referring to FIG. 2, a configuration of a specimen processing system 1 according to this embodiment will be described. FIG. 2 is a block diagram illustrating a configuration of the specimen processing system 1. As illustrated in FIG. 2, the specimen processing system 1 includes a two-arm robot 10, a robot controller 50, and an input device 60. The two-arm robot 10 and the input device 60 are connected to the robot controller 50. As described later, the input device 60 may be omitted.

The two-arm robot 10 includes a right arm and a left arm that are independent of each other. In response to an instruction(s) from the robot controller 50, the two-arm robot 10 performs specimen processing. The two-arm robot 10 is installed in a workroom isolated from the environment to perform the specimen processing.

Figure 3:
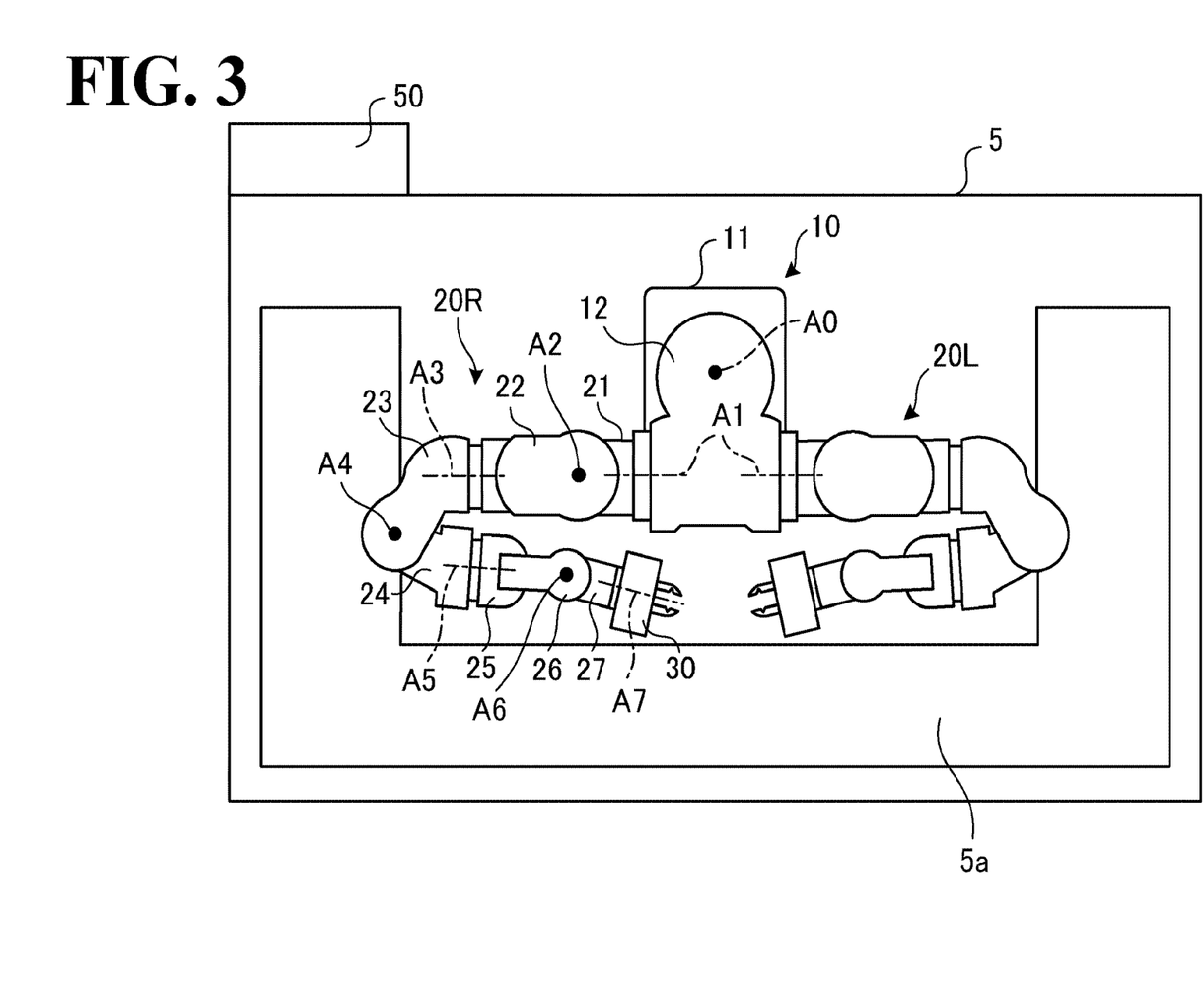
FIG. 3 is a top view of a two-arm robot schematically illustrating a configuration and an arrangement of the two-arm robot.

By referring to FIG. 3, an exemplary configuration and an exemplary arrangement of the two-arm robot 10 will be described. FIG. 3 is a top view of the two-arm robot 10 schematically illustrating a configuration and an arrangement of the two-arm robot 10. As illustrated in FIG. 3, the two-arm robot 10 is installed in a safety cabinet 5. A work table 5a is also disposed in the safety cabinet 5. The robot controller 50 is disposed outside the safety cabinet 5.

The safety cabinet 5 defines an internal space that may be negatively pressurized. By negatively pressurizing the internal space, reagents used in fields such as the biomedical field are kept within the safety cabinet 5 even if the reagents are vaporized. It is also possible to provide in the safety cabinet 5 a misting mechanism to spray the two-arm robot 10 with a cleaning solution such as hydrogen peroxide solution so as to remove a reagent(s) off the two-arm robot 10.

The work table 5a is for specimen-processing tools to rest on. The specimen-processing tools are used when the two-arm robot 10 performs specimen processing such as injection and agitation of reagents, and removal of cells. Examples of the specimen processing tools include, but are not limited to, the spatula 100, the culture vessel 200, test tubes, pipettes, droppers, spoons, and agitators. The specimen processing tools may be placed directly on the work table 5a or may be placed on a jig placed on the work table 5a (for example, spatula stand).

The two-arm robot 10 includes a base 11, a body 12, a right arm 20R, and a left arm 20L. The base 11 is fixed to a surface such as the floor surface of the safety cabinet 5. The body 12 has a base end fixed to the base 11 and a distal end connected to the right arm 20R and the left arm 20L. The body 12 also includes swing axis A0, about which an upper portion of the body 12 swings laterally.

As illustrated in FIG. 3, each of the right arm 20R and the left arm 20L is a multi-articular robot with seven axes that include a redundant axis. The use of a multi-articular robot having a redundant axis ensures more accurate reproduction of details of work performed by an operator. On the distal ends of the right arm 20R and the left arm 20L, the hands 30 are mounted. Each of the hands 30 has a holding mechanism implemented by a movable claw. It is noted that the holding mechanism will not be limited to gripping; any other manner of holding is possible such as adsorbing.

Also as illustrated in FIG. 3, the right arm 20R includes, in increasing order of distance from the base end, a first arm 21, a second arm 22, a third arm 23, a fourth arm 24, a fifth arm 25, a sixth arm 26, and a seventh arm 27. The left arm 20L has an approximately similar configuration to the configuration of the right arm 20R and therefore will not be elaborated here.

The first arm 21 has its base end supported by the body 12 and is turnable about first axis A1. The second arm 22 has its base end supported by the distal end of the first arm 21 and is swingable about second axis A2. The third arm 23 has its base end supported by the distal end of the second arm 22 and is turnable about third axis A3. The fourth arm 24 has its base end supported by the distal end of the third arm 23 and is swingable about fourth axis A4.

The fifth arm 25 has its base end supported by the distal end of the fourth arm 24 and is turnable about fifth axis A5. The sixth arm 26 has its base end supported by the distal end of the fifth arm 25 and is swingable about sixth axis A6. The seventh arm 27 has its base end supported by the distal end of the sixth arm 26 and is turnable about seventh axis A7. The hand 30 is supported by the distal end of the seventh arm 27.

The term "swing" found in "swingable" in the above description refers to a movement that involves changes in the angle formed by adjoining arms. The term "turn" found in "turnable" refers to a relative movement that does not involve changes in the angle formed by adjoining arms.

The two-arm robot 10 causes the right arm 20R and the left arm 20L to cooperate with each other to perform the removal operation illustrated in FIG. 1 with, for example, the hand 30 of the right arm 20R holding the spatula 100 and the hand 30 of the left arm 20L holding the culture vessel 200. This configuration makes the removal operation on the circumferential side 201a more reliable and more accurate. In another possible embodiment, the two-arm robot 10 may hold one of the spatula 100 and the culture vessel 200, with the other one of the spatula 100 and the culture vessel 200 being fixed to the work table 5a or anywhere else to perform the removal operation.

Referring again to FIG. 2, the robot controller 50 will be described. The robot controller 50 includes a controller 51 and a storage 52. The controller 51 includes a determiner 51a, a switch 51b, and an operation controller 51c. The storage 52 stores classified information 52a and teaching information 52b.

The robot controller 50 includes a computer and various circuits. The computer includes CPU (Central Processing Unit), ROM (Read Only Memory), RAM (Random Access Memory), HDD (Hard Disk Drive), and an input/output port.

The CPU of the computer reads programs stored in the ROM and executes the programs, and thus functions as the determiner 51a, the switch 51b, and the operation controller 51c of the controller 51.

Alternatively, at least one or all of the determiner 51a, the switch 51b, and the operation controller 51c may be made up of hardware such as ASIC (Application Specific Integrated Circuit) and FPGA (Field Programmable Gate Array).

The storage 52 corresponds to the RAM and the HDD. The RAM and the HDD are capable of storing the classified information 52a and the teaching information 52b. In another possible embodiment, the robot controller 50 may obtain the above-described programs and the various kinds of information from another computer connected to the robot controller 50 through a wired or wireless network or from a portable recording medium.

The controller 51 controls the operation of the two-arm robot 10. Based on the classification of the cells that are on the culture vessel 200 and that are to undergo the removal operation, the determiner 51a determines whether to perform the removal operation in "outer-end leading posture" or "inner-end leading posture".

Specifically, the determiner 51a receives from the input device 60 an identifier or a similar indicator that indicates the classification of the cells. Then, the determiner 51a compares the received identifier with the classified information 52a stored in the storage 52. The classified information 52a is information that correlates the identifier with a posture (outer-end leading posture or inner-end leading posture).

The determiner 51a searches the classified information 52a for the received identifier to find out which posture, outer-end leading posture or inner-end leading posture, the received identifier is correlated with. Then, the determiner 51a informs the switch 51b of the posture found as a result of the search.

Examples of the input device 60 include, but are not limited to, a terminal such as a pendant of the robot controller 50, an input device such as a keyboard and a touch panel display, and a computer connected to the robot controller 50 through a wire or wirelessly. In another possible embodiment, the input device 60 may be a bar code scanner to read a bar code that is attached to the culture vessel 200 and that indicates a cell classification.

In still another possible embodiment, the input device 60 may be omitted. When the input device 60 is omitted, the determiner 51a may determine which posture, outer-end leading posture or inner-end leading posture, to use with respect to a plurality of culture vessels 200 according to a predetermined order. It will be readily appreciated that either outer-end leading posture or inner-end leading posture alone may be used with respect to the plurality of culture vessels 200.

Based on the determination made by the determiner 51a, the switch 51b switches the order of "jobs" of the teaching information 52b. The teaching information 52b contains "jobs" that constitute a program defining a movement path for the two-arm robot 10. The program is prepared during teaching the two-arm robot 10 how to move.

When the cells nearer the circumference of the culture surface 201 are removed in outer-end leading posture, the switch 51b switches the order of the jobs by putting the removal operation on the internal side after the removal operation on the circumferential side. When the cells nearer the circumference of the culture surface 201 are removed in inner-end leading posture, the switch 51b switches the order of the jobs by putting the removal operation on the circumferential side after the removal operation on the internal side. This configuration shortens the time necessary to generate the "jobs" and simplifies the work necessary to generate the "jobs".

Based on the teaching information 52b having the order of jobs switched by the switch 51b, the operation controller 51c instructs the actuators (not illustrated) built in the joints of the two-arm robot 10 to implement a desired posture of the two-arm robot 10. The operation controller 51c also improves the accuracy of the operation performed by the two-arm robot 10 by, for example, performing feedback control using encoder values obtained from the actuators.

Figure 4A:
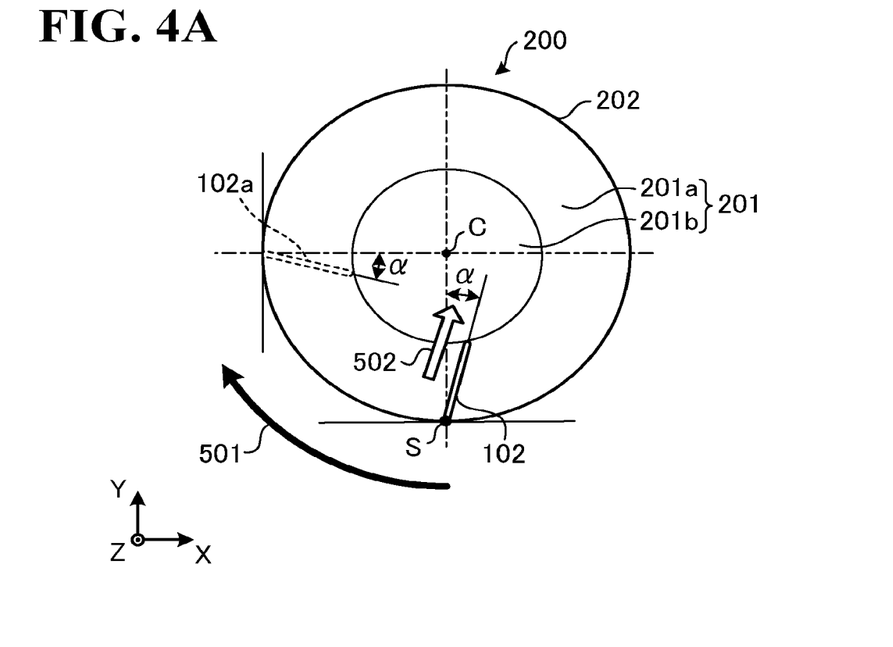
FIG. 4A schematically illustrates a removal operation on a circumferential side in outer-end leading posture.
Figure 4B:
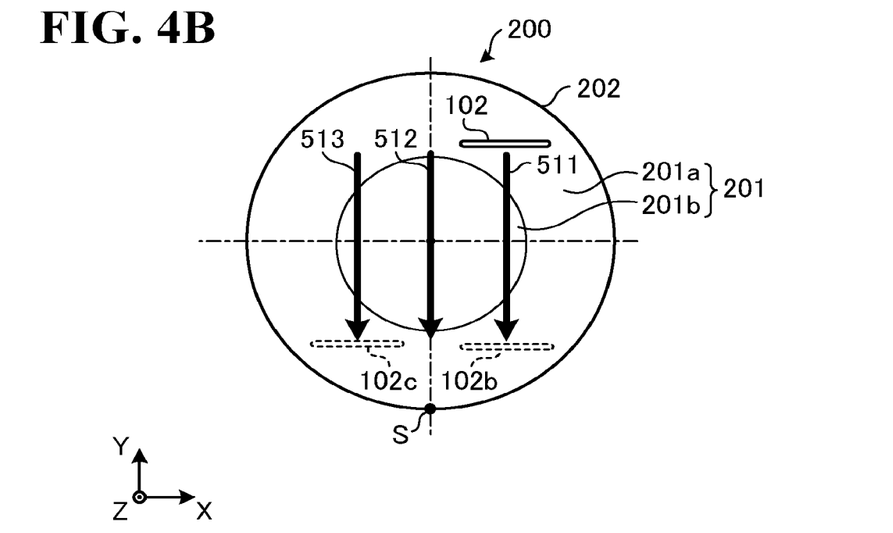
FIG. 4B schematically illustrates a removal operation on an internal side in outer-end leading posture.

By referring to FIGS. 4A and 4B, the removal operation in outer-end leading posture performed by the specimen processing system 1 will be described. FIG. 4A schematically illustrates a removal operation on the circumferential side 201a in outer-end leading posture. FIG. 4B schematically illustrates an removal operation on the internal side 201b in outer-end leading posture. It is noted that FIGS. 4A and 4B are top views of the culture vessel 200, as seen from the open side of the culture vessel 200, that is, from the Z-axis positive direction.

Also as illustrated in FIGS. 4A and 4B, the removal operation on the circumferential side 201a of the culture surface 201 in outer-end leading posture is first performed on the circumferential side 201a of the culture surface 201 as illustrated in FIG. 4A, and then performed on the internal side 201b of the culture surface 201 as illustrated in FIG. 4B.

As illustrated in FIG. 4A, in the removal operation on the circumferential side 201a of the culture surface 201 in outer-end leading posture, which is performed in the forward direction 501, the second end of the blade 102 (the end nearer the center C) is displaced clockwise at an angle of α from the radial direction of the culture vessel 200 relative to the first end of the blade 102 (the end on the surrounding wall 202), so that the blade 102 is inclined clockwise at an angle of α.

Then, the spatula 100 makes one revolution from the start position S to the start position S while keeping the blade 102 inclined at an angle of α. For reference purposes, posture 102a is illustrated in broken lines in FIG. 4A indicating a posture of the blade 102 moved clockwise by 90 degrees from the start position S.

In the removal operation with the blade 102 taking outer-end leading posture, cells removed by the blade 102 are moved in cell movement direction 502. In the embodiment of FIG. 4A, the cell movement direction 502 is toward the internal side 201b of the culture surface 201.

That is, instead of remaining on the forward side of the blade 102 in the forward direction 501, the removed cells move in the cell movement direction 502 along the blade 102 and end up being collected on the internal side 201b of the culture surface 201. Even if the cells are fragile or difficult to remove, the above configuration enables the cells to be collected on the internal side 201b with no or minimized damage to the cells.

The removal operation on the circumferential side 201a of the culture surface 201 starts at the start position S illustrated in FIG. 4A and makes the spatula 100 make one revolution clockwise to return to the start position S. That is, the start position S is also an end position of the removal operation. Making one revolution in the removal operation in this manner makes the removal operation on the circumferential side 201a more reliable.

While in this embodiment the removal operation on the circumferential side 201a of the culture surface 201 makes the spatula 100 make one revolution (360 degrees) along the circumference of the culture surface 201, it is possible to make the spatula 100 make more than one revolution. Making more than one revolution makes the cell removal on the circumferential side 201a of the culture surface 201 even more reliable.

The removal operation on the circumferential side 201a of the culture surface 201 in outer-end leading posture is followed by the removal operation on the internal side 201b of the culture surface 201 illustrated in FIG. 4B.

The removal operation on the internal side 201b first makes the spatula 100 move approximately straight in forward direction 511, in which the spatula 100 moves, with the blade 102 perpendicular to the forward direction 511. This operation is performed a plurality of times with the start position of each operation being displaced in the X-axis negative direction. While in FIG. 4B the removal operation on the internal side 201b is performed three times, it is possible to optimize the number of removal operations based on the area of the culture surface 201 of the culture vessel 200 or the length of the blade 102 of the spatula 100.

As illustrated in FIG. 4B, forward directions 511, 512, and 513 are toward the end point of each removal operation on the circumferential side 201a, that is, toward start point S illustrated in FIG. 4B. Performing the removal operations on the internal side 201b in the forward directions 511, 512, and 513 makes cell collection more efficient. While in this embodiment each removal operation on the internal side 201b makes the spatula 100 move approximately straight in the forward directions 511, 512, and 513, the path of the removal operation on the internal side 201b will not be limited to the above-described linear path. Other possible examples of the path include, but are not limited to, a curved path and a combination of a linear path and a curve path.

The range of the removal operation on the internal side 201b performed by the blade 102 overlaps the region covered by the removal operation on the circumferential side 201a. This causes those cells, if any, that have escaped the removal operation on the circumferential side 201a to be reliably collected in the removal operations on the internal side 201b. For reference purposes, the end position, 102b, of the removal operation performed in the forward direction 511 is illustrated in FIG. 4B. The end position 102b is within the region covered by the removal operation on the circumferential side 201a of the culture surface 201.

A second removal operation on the internal side 201b makes the spatula 100 move in the forward direction 512, similarly to the movement in the forward direction 511. The range covered by the removal operation performed by the blade 102 in the forward direction 512 overlaps the range covered by the removal operation performed by the blade 102 in the forward direction 511. This configuration makes the cells on the internal side 201b more reliably removed.

In a manner similar to the manner in which the second removal operation has been performed on the internal side 201b, a third removal operation is performed on the internal side 201b in the forward direction 513. For reference purposes, the end position, 102c, of the removal operation performed in the forward direction 513 is illustrated in FIG. 4B. Thus, after the removal operation on the circumferential side 201a in outer-end leading posture illustrated in FIG. 4A, the removal operation on the internal side 201b illustrated in FIG. 4B is performed. This configuration ensures that cells that are fragile or difficult to remove are collected to one position with no or minimized damage to the cells.

Figure 5:
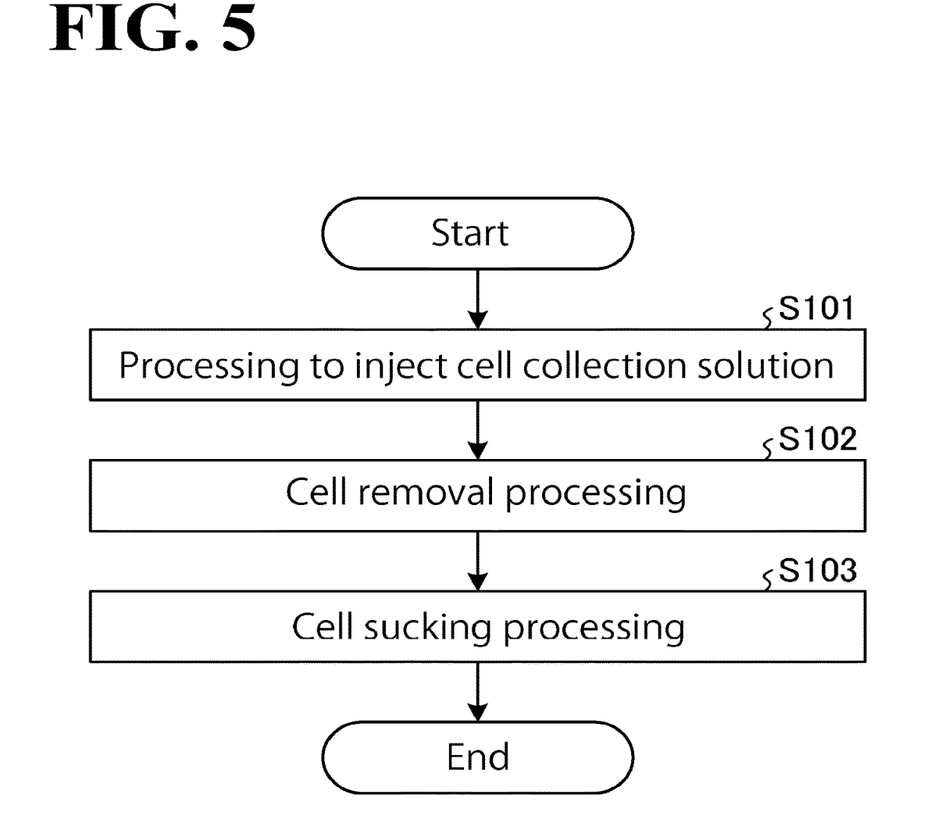
FIG. 5 is a flowchart of a procedure for processings performed by the specimen processing system.

By referring to FIG. 5, a procedure for processings performed by the specimen processing system 1 will be described. FIG. 5 is a flowchart of a procedure for processings performed by the specimen processing system 1. First, in response to an instruction from the robot controller 50, the two-arm robot 10 injects a cell collection solution into the culture vessel 200 (step S101).

For example, the two-arm robot 10 holds a dropper in the hand 30 of one arm of the two-arm robot 10 and holds the culture vessel 200 in the hand 30 of the other arm of the two-arm robot 10. Then, the two-arm robot 10 makes the dropper suck the cell collection solution and inject the sucked cell collection solution into the culture vessel 200.

Next, the two-arm robot 10 performs cell removal processing (step S102). For example, the two-arm robot 10 causes its arms to cooperate with each other to perform the cell removal processing with the one arm replacing the dropper with the spatula 100. Details of the processing at step S102 will be described later by referring to FIG. 6.

At step S103, the two-arm robot 10 performs sucking processing with respect to the cells removed at step S102, and thus the processings end. For example, the two-arm robot 10 replaces the spatula 100 with a dropper to suck the cells collected at one position on the culture vessel 200. Then, the two-arm robot 10 causes the dropper to discharge the sucked cells into a test tube.

Figure 6:
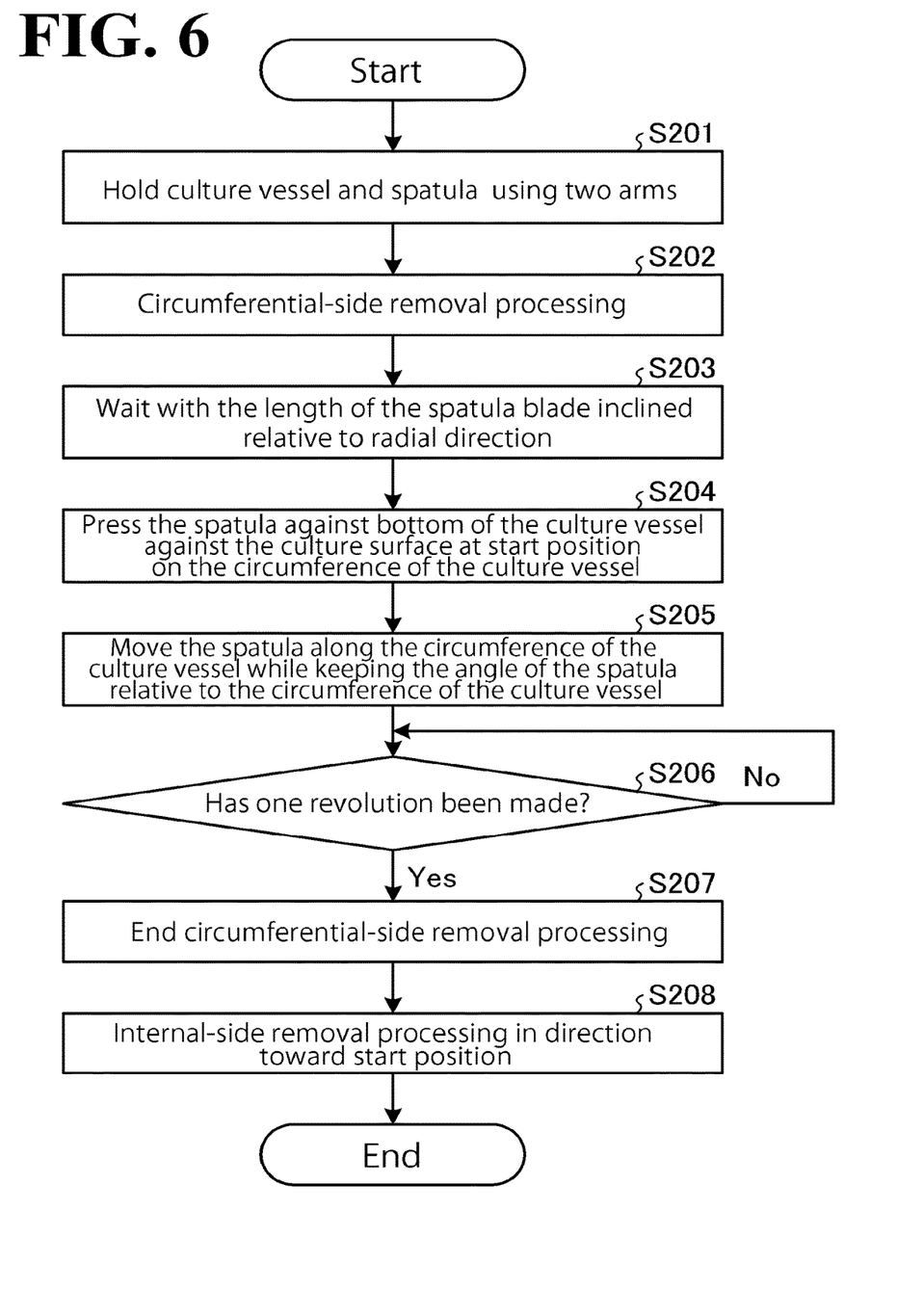
FIG. 6 is a flowchart of a procedure for cell removal processing.

By referring to FIG. 6, description will be made with regard to details of the procedure for the cell removal processing at step S102 described in FIG. 5. FIG. 6 is a flowchart of a procedure for the cell removal processing. The two-arm robot 10 holds the culture vessel 200 and the spatula 100 respectively by the two arms (step S201).

Next, the two-arm robot 10 starts the removal processing on the circumferential side 201a of the culture surface 201 illustrated in FIG. 4A (step S202). First, the two-arm robot 10 waits with the length of the blade 102 of the spatula 100 inclined relative to the radial direction of the culture vessel 200 (step S203). Specifically, the spatula 100 is kept in outer-end leading posture.

Then, at the start position S (see FIG. 4A), which is on the circumference of the culture vessel 200, the two-arm robot 10 presses the spatula 100 against the bottom of the culture vessel 200 (against the culture surface 201) (step S204). Then, the two-arm robot 10 moves the spatula 100 along the circumference of the culture vessel 200 while keeping the angle of the spatula 100 relative to the circumference of the culture vessel 200 (step S205).

Next, the specimen processing system 1 determines whether the spatula 100 has made one revolution along the circumference of the culture vessel 200 (step S206). When the specimen processing system 1 determines that the spatula 100 has not made one revolution (No at step S206 No), the specimen processing system 1 repeats the determination processing at step S206. When the specimen processing system 1 determines that the spatula 100 has made one revolution (Yes at step S206), the specimen processing system 1 ends the circumferential-side removal processing (step S207).

Then, the two-arm robot 10 performs, in the direction toward the start position S (see FIG. 4B), the removal processing on the internal side 201b of the culture surface 201, as illustrated in FIG. 4B (step S208), and the processings end.

Figure 7:
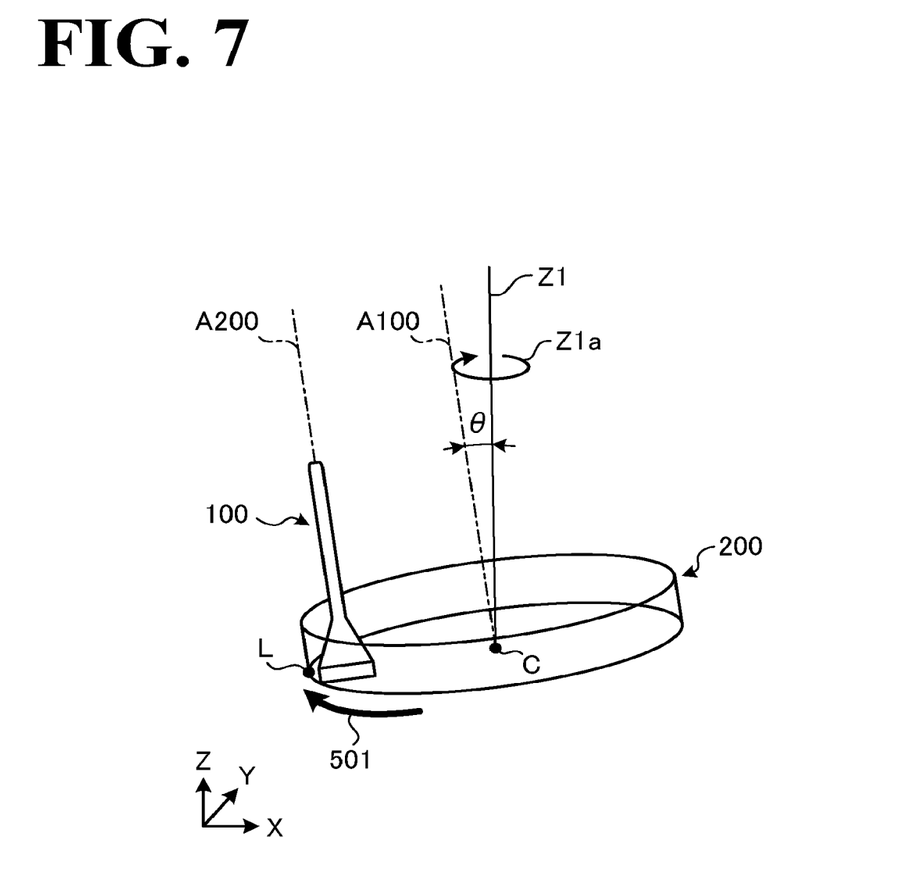
FIG. 7 illustrates a cooperation between two arms of a two-arm robot.

By referring to FIG. 7, an exemplary cooperation between the two arms of the two-arm robot 10 will be described. FIG. 7 illustrates a cooperation between the two arms of the two-arm robot 10. It the following description, the two-arm robot 10 holds the spatula 100 in the hand 30 of one arm and holds the culture vessel 200 in the hand 30 of the other arm.

Also in FIG. 7, the removal operation on the circumferential side described in FIG. 4A is performed while the culture vessel 200 is inclined in different directions. As illustrated in FIG. 7, the arm of the two-arm robot 10 holding the culture vessel 200 changes the inclination of the culture vessel 200 to keep lowermost point L of the culture vessel 200 more frontward than the spatula 100 in the forward direction 501, in which the spatula 100 moves.

Specifically, the one arm holding the spatula 100 performs the operation illustrated in FIG. 1, making the spatula 100 make orbital rotation about the center line A100 of the culture vessel 200 while rotating itself about the rotation axis A200. Simultaneously, the other arm changes the inclination of the culture vessel 200.

In the embodiment of FIG. 7, the culture vessel 200 circumnutates in direction Z1a with the center line A100 of the culture vessel 200 inclined at an angle of $\theta$ relative to line Z1, which is parallel to Z axis. This ensures that cells removed from the culture surface 201 or cells floating off the culture surface 201 are kept in front of the spatula 100 in the forward direction 501, resulting in improved cell collection efficiency. Angle $\theta$ may be any angle greater than zero degree.

Figure 8A:
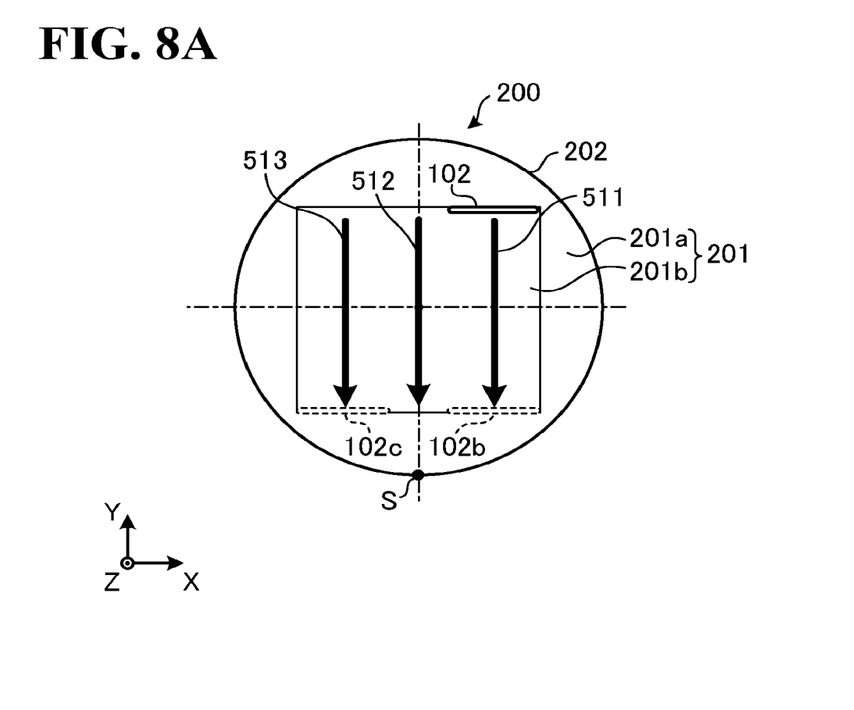
FIG. 8A schematically illustrates a removal operation on the internal side in inner-end leading posture.
Figure 8B:
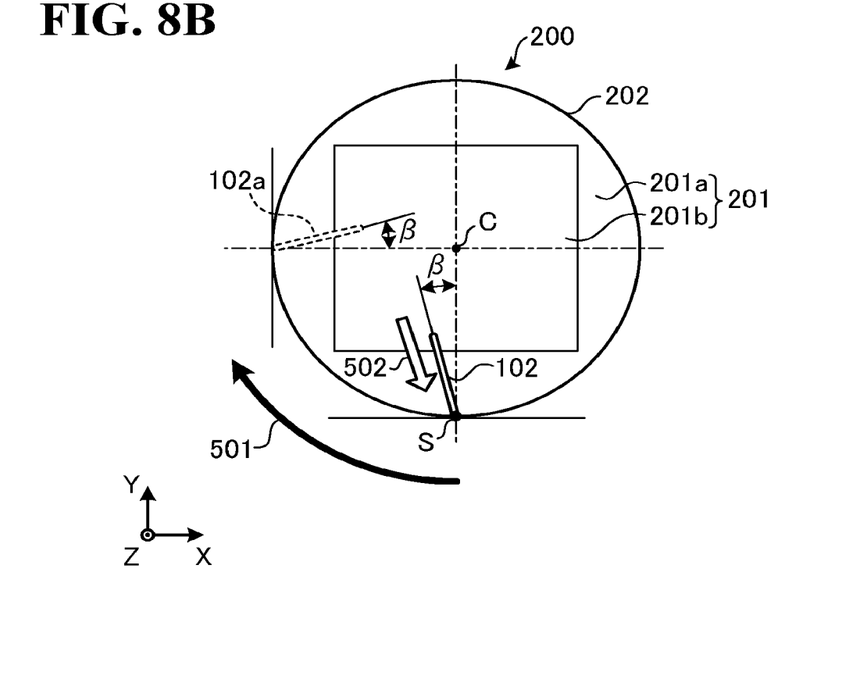
FIG. 8B schematically illustrates a removal operation on the circumferential side in inner-end leading posture.

By referring to FIGS. 8A and 8B, the removal operation in inner-end leading posture performed by the specimen processing system 1 will be described. FIG. 8A schematically illustrates the removal operation on the internal side in inner-end leading posture. FIG. 8B schematically illustrates the removal operation on the circumferential side in inner-end leading posture. FIGS. 8A and 8B are top views of the culture vessel 200, as seen from the open side of the culture vessel 200, that is, from the Z-axis positive direction.

As illustrated in FIGS. 8A and 8B, when the spatula 100 is in inner-end leading posture in the removal operation on the circumferential side 201a of the culture surface 201, as illustrated in FIG. 8B, the removal operation on the internal side 201b of the culture surface 201 illustrated in FIG. 8A is first to be performed, followed by the removal operation on the circumferential side 201a of the culture surface 201 in inner-end leading posture.

As illustrated in FIG. 8A, the removal operation on the internal side 201b of the culture surface 201 is similar to the removal operation on the internal side 201b illustrated in FIG. 4B. As illustrated in FIG. 8A, the internal side 201b is defined by a rectangle that corresponds to the region covered by the internal-side removal operation. The internal-side removal operation illustrated in FIG. 8A is similar to the internal-side removal operation illustrated FIG. 4B and will not be elaborated here.

The removal operation on the internal side 201b of the culture surface 201 is followed by the removal operation on the circumferential side 201a of the culture surface 201, as illustrated in FIG. 8B.

As illustrated in FIG. 8B, in the removal operation on the circumferential side 201a of the culture surface 201 in inner-end leading posture, which is performed in the forward direction 501, the second end of the blade 102 (the end nearer the center C) is displaced anti-clockwise at an angle of β from the radial direction of the culture vessel 200 relative to the first end of the blade 102 (the end on the surrounding wall 202), so that the blade 102 is inclined anti-clockwise at an angle of β.

Then, the spatula 100 makes one revolution from the start position S to the start position S while keeping the blade 102 inclined at an angle of β. For reference purposes, the posture 102a is illustrated in broken lines in FIG. 8B indicating a posture of the blade 102 moved clockwise by 90 degrees from the start position S.

In the removal operation with the blade 102 taking inner-end leading posture, cells removed by the blade 102 are moved in cell movement direction 502. In the embodiment of FIG. 8B, the cell movement direction 502 is toward the circumferential side 201a of the culture surface 201. That is, the removed cells move in the cell movement direction 502 along the blade 102 and end up being collected on or near the surrounding wall 202 in front of the blade 102 in the forward direction 501. This configuration improves efficiency in collecting cells to one position.

The removal operation on the circumferential side 201a of the culture surface 201 starts at the start position S illustrated in FIG. 8B and makes the spatula 100 make one revolution clockwise to return to the start position S. That is, the start position S is also an end position of the removal operation.

While in this embodiment the removal operation on the circumferential side 201a of the culture surface 201 makes the spatula 100 make one revolution (360 degrees) along the circumference of the culture surface 201, it is possible to make the spatula 100 make more than one revolution. Making more than one revolution makes the cell removal on the circumferential side 201a of the culture surface 201 even more reliable.

Figure 9:
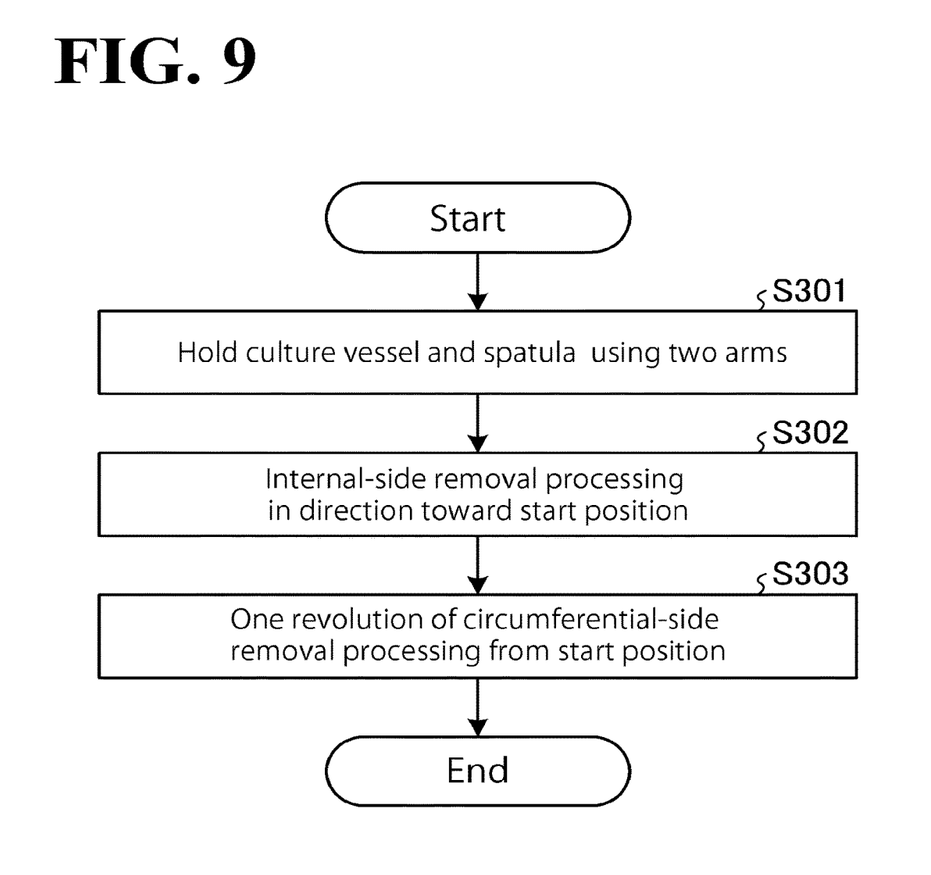
FIG. 9 is a flowchart of a procedure for cell removal processing in inner-end leading posture.

By referring to FIG. 9, description will be made with regard to details of the procedure for the cell removal processing at step S102 described in FIG. 5 in the case of the blade 102 taking inner-end leading posture. FIG. 9 is a flowchart of a procedure for the cell removal processing in inner-end leading posture. The two-arm robot 10 holds the culture vessel 200 and the spatula 100 respectively by the two arms (step S301).

Then, the two-arm robot 10 performs the internal-side removal processing in the direction toward the start position S (see FIG. 8B) of the circumferential-side removal processing (step S302). Then, with the spatula 100 taking inner-end leading posture, the two-arm robot 10 performs one revolution of the circumferential-side removal processing from the start position S (step S303), and the processings end. Details of the procedure at step S303 are similar to the procedure at step S202 through step S207 illustrated in FIG. 6 and will not be elaborated here.

As has been described hereinbefore, the specimen processing system 1 according to this embodiment includes the culture vessel 200, the spatula 100, the robot 10, and the robot controller 50. The culture vessel 200 is open on the top surface of the culture vessel 200 and includes the culture surface 201, which has a circular shape and on which cells are culturable. The spatula 100 includes the blade 102, which removes the cells off the culture surface 201. The robot 10 includes the hands 30, which are capable of holding at least one of the culture vessel 200 and the spatula 100. The robot controller 50 controls the robot 10.

The robot controller 50 includes the operation controller 51c. The operation controller 51c controls the robot 10 to perform a first operation. In the first operation, the robot 10 moves the spatula 100 relative to the culture vessel 200 with the first end of the blade 102 on the circumference of the culture surface 201 so as to remove cells on the circumferential side 201a of the culture surface 201. Then, the operation controller 51c controls the robot 10 to perform a second operation. In the second operation, the robot 10 moves the spatula 100 relative to the culture vessel 200 so as to remove cells on the internal side 201b of the culture surface 201.

The specimen processing system 1 according to this embodiment makes a gap difficult to occur between the blade 102 of the spatula 100 and the culture vessel 200, and thus improves cell collection efficiency. Also, the specimen processing system 1 performs the removal operation on the circumferential side 201a of the culture surface 201 using the spatula 100 in outer-end leading posture. This configuration improves efficiency in collecting cells with no or minimized damage to the cells even if the cells are fragile.

While in the above-described embodiments the spatula 100 moves clockwise relative to the culture vessel 200 in plan view of the culture vessel 200, the spatula 100 may move anti-clockwise.

Obviously, numerous modifications and variations of the present disclosure are possible in light of the above teachings. It is therefore to be understood that within the scope of the appended claims, the present disclosure may be practiced otherwise than as specifically described herein.

What is claimed as new and desired to be secured by Letters Patent of the United States is:

1. A specimen processing system, comprising:
a culture vessel comprising a culture surface in a circular shape;
a spatula comprising a blade configured to remove cells cultured in the culture vessel off the culture surface of the culture vessel;
a robot comprising a hand structure configured to hold at least one of the culture vessel and the spatula; and
a robot controller comprising circuitry configured to move the spatula relative to the culture vessel with a first end of the blade on a circumference of the culture surface such that the spatula removes first cells nearer the circumference of the culture surface from the cells on the culture surface, and to move the spatula relative to the culture vessel such that the spatula removes second cells on an inner side with respect to the first cells from the cells on the culture surface.

2. The specimen processing system according to claim 1, wherein the circuitry of the robot controller is configured to control the robot such that the blade removes the first cells while keeping the blade inclined relative to a radial direction of the culture vessel with a second end of the blade being displaced from the radial direction relative to the first end of the blade in a backward direction opposite to a forward direction in which the spatula moves.

3. The specimen processing system according to claim 1, wherein the circuitry of the robot controller is configured to control the robot such that the blade makes at least one revolution along the circumference of the culture surface before the removing of the second cells.

4. The specimen processing system according to claim 1, wherein the circuitry of the robot controller is configured to make a direction in which the second cells are removed a direction toward a position at which the first operation has ended.

5. The specimen processing system according to claim 1, wherein the hand structure of the robot comprises two arms each comprising a hand, and the circuitry of the robot controller is configured to control the robot such that the blade removes the first cells by holding the spatula with the hand of one arm while holding the culture vessel with the hand of the other arm.

6. The specimen processing system according to claim 2, wherein the circuitry of the robot controller is configured to control the robot such that the blade makes at least one revolution along the circumference of the culture surface before the removing of the second cells.

7. The specimen processing system according to claim 2, wherein the circuitry of the robot controller is configured to make a direction in which the second cells are removed a direction toward a position at which the first operation has ended.

8. The specimen processing system according to claim 3, wherein the circuitry of the robot controller is configured to make a direction in which the second cells are removed a direction toward a position at which the first operation has ended.

9. The specimen processing system according to claim 6, wherein the circuitry of the robot controller is configured to make a direction in which the second cells are removed a direction toward a position at which the first operation has ended.

10. The specimen processing system according to claim 2, wherein the hand structure of the robot comprises two arms each comprising a hand, and the circuitry of the robot controller is configured to control the robot such that the blade removes the first cells by holding the spatula with the hand of one arm while holding the culture vessel with the hand of the other arm.

11. The specimen processing system according to claim 3, wherein the hand structure of the robot comprises two arms each comprising a hand, and the circuitry of the robot controller is configured to control the robot such that the blade removes the first cells by holding the spatula with the hand of one arm while holding the culture vessel with the hand of the other arm.

12. The specimen processing system according to claim 4, wherein the hand structure of the robot comprises two arms each comprising a hand, and the circuitry of the robot controller is configured to control the robot such that the blade removes the first cells by holding the spatula with the hand of one arm while holding the culture vessel with the hand of the other arm.

13. The specimen processing system according to claim 6, wherein the hand structure of the robot comprises two arms each comprising a hand, and the circuitry of the robot controller is configured to control the robot such that the blade removes the first cells by holding the spatula with the hand of one arm while holding the culture vessel with the hand of the other arm.

14. The specimen processing system according to claim 7, wherein the hand structure of the robot comprises two arms each comprising a hand, and the circuitry of the robot controller is configured to control the robot such that the blade removes the first cells by holding the spatula with the hand of one arm while holding the culture vessel with the hand of the other arm.

15. The specimen processing system according to claim 8, wherein the hand structure of the robot comprises two arms each comprising a hand, and the circuitry of the robot controller is configured to control the robot such that the blade removes the first cells by holding the spatula with the hand of one arm while holding the culture vessel with the hand of the other arm.

16. The specimen processing system according to claim 9, wherein the hand structure of the robot comprises two arms each comprising a hand, and the circuitry of the robot controller is configured to control the robot such that the blade removes the first cells by holding the spatula with the hand of one arm while holding the culture vessel with the hand of the other arm.

17. A specimen processing system, comprising:
a culture vessel comprising a culture surface in a circular shape;
a spatula comprising a blade configured to remove cells cultured on the culture surface off the culture surface of the culture vessel;
a robot comprising a hand structure configured to hold at least one of the culture vessel and the spatula; and
a robot controller comprising circuitry configured to move the spatula relative to the culture vessel while keeping the blade inclined relative to a radial direction of the culture vessel with a first end of the blade on a circumference of the culture surface and with a second end of the blade displaced from the radial direction relative to the first end of the blade such that the blade removes first cells nearer the circumference of the culture surface from the cells cultured on the culture surface.

18. The specimen processing system according to claim 17, wherein the circuitry of the robot controller is configured to displace the second end of the blade from the radial direction relative to the first end of the blade in a backward direction opposite to a forward direction in which the spatula moves such that the blade removes the first cells, and move the spatula relative to the culture vessel such that the blade removes second cells on an inner side with respect to the first cells on the culture surface from the cells cultured on the culture surface.

19. The specimen processing system according to claim 17, wherein the circuitry of the robot controller is configured to move the spatula relative to the culture vessel such that the blade removes second cells on inner than the first cells on the culture surface from the cells cultured on the culture surface, and displace the second end of the blade from the radial direction relative to the first end of the blade in the forward direction in which the spatula moves such that the blade removes the first cells.

20. A method for processing a specimen, comprising:
controlling a robot comprising a hand structure configured to hold at least one of a culture vessel having a culture surface in a circular shape and a spatula having a blade such that the robot moves the spatula relative to the culture vessel with a first end of the blade on a circumference of the culture surface of the culture vessel and that a blade of the spatula removes first cells nearer the circumference of the culture surface from the cell cultured on the culture surface of the culture vessel; and
controlling the robot such that the spatula moves relative to the culture vessel and that the blade removes second cells on an inner side with respect to the first cells from the cell cultured on the culture surface of the culture vessel.

* * * * *